(12) United States Patent
Kuyava et al.

(10) Patent No.: US 9,402,723 B2
(45) Date of Patent: Aug. 2, 2016

(54) PENILE PROSTHESIS IMPLANTATION DEVICE

(71) Applicant: AMS Research, LLC, Minnetonka, MN (US)

(72) Inventors: Charles C. Kuyava, Eden Prairie, MN (US); Gary Rocheleau, Maple Grove, MN (US)

( * ) Notice: Subject to any disclaimer, the term of this patent is extended or adjusted under 35 U.S.C. 154(b) by 0 days.

(21) Appl. No.: 14/656,911

(22) Filed: Mar. 13, 2015

(65) Prior Publication Data

US 2015/0182339 A1    Jul. 2, 2015

Related U.S. Application Data

(63) Continuation of application No. 14/337,926, filed on Jul. 22, 2014, now Pat. No. 9,005,111, which is a continuation of application No. 14/037,797, filed on Sep. 26, 2013, now Pat. No. 8,864,651, which is a continuation of application No. 12/644,805, filed on Dec. 22, 2009, now Pat. No. 8,545,391.

(60) Provisional application No. 61/140,173, filed on Dec. 23, 2008, provisional application No. 61/140,350, filed on Dec. 23, 2008.

(51) Int. Cl.
    *A61F 2/26*      (2006.01)

(52) U.S. Cl.
    CPC ........... *A61F 2/26* (2013.01); *A61F 2250/0065* (2013.01)

(58) Field of Classification Search
    CPC ........... A61B 17/0482; A61B 17/2926; A61B 2017/2932; A61B 2017/2933; A61B 2017/2926; A61B 2017/2917; A61B 2017/2916; A61B 2017/2915; A61B 2017/2913; A61B 2017/2912; A61B 2017/2902; A61B 2017/2901; A61F 2/26
    USPC .............. 600/38–41; 606/139, 144, 147, 225, 606/205–209
See application file for complete search history.

(56) References Cited

U.S. PATENT DOCUMENTS

| | | | |
|---|---|---|---|
| 525,020 A | 8/1894 | Jungner | |
| 734,498 A | 7/1903 | Bachler | |
| 2,455,859 A | 12/1948 | Foley | |
| 2,533,924 A | 12/1950 | Foley | |
| 3,404,677 A * | 10/1968 | Springer | ........................ 600/564 |
| 3,538,917 A | 11/1970 | Selker | |
| 3,642,005 A | 2/1972 | McGinnis | |
| 3,720,200 A | 3/1973 | Laird | |
| 3,744,063 A | 7/1973 | McWhorter et al. | |
| 3,750,194 A | 8/1973 | Summers | |

(Continued)

OTHER PUBLICATIONS

U.S. Appl. No. 60/988,264, filed Nov. 15, 2007.

(Continued)

*Primary Examiner* — Samuel Gilbert

(57) ABSTRACT

A penile prosthesis implantation device includes a barrel having a bore, and an obturator that is received within the bore and is configured to slide along a longitudinal axis of the bore relative to the barrel. A distal end of the obturator includes a needle clamp and one or more bore engaging members. The needle clamp is configured to hold a thread attachment end of a needle. Each bore engaging member includes a surface that engages an interior wall of the bore. A gap extends between a central portion of the obturator and the one or more bore engaging members.

9 Claims, 7 Drawing Sheets

(56) References Cited

U.S. PATENT DOCUMENTS

| | | |
|---|---|---|
| 3,853,122 A | 12/1974 | Strauch et al. |
| 3,863,622 A | 2/1975 | Buuck |
| 4,201,202 A | 5/1980 | Finney et al. |
| 4,222,377 A | 9/1980 | Burton |
| 4,244,370 A | 1/1981 | Furlow et al. |
| 4,267,829 A | 5/1981 | Burton et al. |
| 4,342,308 A | 8/1982 | Trick |
| 4,353,360 A | 10/1982 | Finney et al. |
| 4,360,010 A | 11/1982 | Finney |
| RE31,121 E | 1/1983 | Reinicke |
| 4,383,525 A | 5/1983 | Scott et al. |
| 4,386,601 A | 6/1983 | Trick |
| 4,408,597 A | 10/1983 | Tenney, Jr. |
| 4,412,530 A | 11/1983 | Burton |
| 4,417,567 A | 11/1983 | Trick |
| 4,419,985 A | 12/1983 | Trick |
| 4,502,159 A | 3/1985 | Woodroof et al. |
| 4,523,584 A | 6/1985 | Yachia et al. |
| 4,549,531 A | 10/1985 | Trick |
| 4,550,720 A | 11/1985 | Trick |
| 4,553,533 A | 11/1985 | Leighton |
| 4,558,693 A | 12/1985 | Lash et al. |
| 4,566,446 A | 1/1986 | Fogarty |
| 4,584,990 A | 4/1986 | Haber et al. |
| 4,634,443 A | 1/1987 | Haber |
| 4,682,583 A | 7/1987 | Burton et al. |
| 4,708,140 A | 11/1987 | Baron |
| 4,829,990 A | 5/1989 | Thuroff et al. |
| 4,834,115 A | 5/1989 | Stewart |
| 4,865,030 A | 9/1989 | Polyak |
| 4,878,889 A | 11/1989 | Polyak |
| 4,896,678 A | 1/1990 | Ogawa |
| 4,969,474 A | 11/1990 | Schwarz |
| 4,994,020 A | 2/1991 | Polyak |
| 5,012,822 A | 5/1991 | Schwarz |
| 5,013,292 A | 5/1991 | Lemay |
| 5,050,592 A | 9/1991 | Olmedo |
| 5,078,676 A | 1/1992 | Bailly |
| 5,088,980 A | 2/1992 | Leighton |
| 5,097,848 A | 3/1992 | Schwarz |
| 5,242,458 A * | 9/1993 | Bendel et al. ............... 606/147 |
| 5,370,690 A | 12/1994 | Barrett |
| 5,562,598 A | 10/1996 | Whalen et al. |
| 5,570,690 A | 11/1996 | Yoon |
| 5,628,757 A * | 5/1997 | Hasson .................... 606/148 |
| 5,634,878 A | 6/1997 | Grundei |
| 5,782,916 A | 7/1998 | Pintauro et al. |
| 5,797,958 A * | 8/1998 | Yoon ..................... 606/207 |
| 5,851,176 A | 12/1998 | Willard |
| 5,868,729 A | 2/1999 | Pelfrey |
| 5,893,826 A | 4/1999 | Salama |
| 5,989,288 A | 11/1999 | Pintauro et al. |
| 6,013,102 A | 1/2000 | Pintauro et al. |
| 6,063,119 A | 5/2000 | Pintauro et al. |
| 6,066,174 A | 5/2000 | Farris |
| 6,095,969 A | 8/2000 | Karram et al. |
| 6,171,233 B1 | 1/2001 | Willard |
| 6,183,520 B1 | 2/2001 | Pintauro et al. |
| 6,328,687 B1 | 12/2001 | Karram et al. |
| 6,354,991 B1 | 3/2002 | Gross et al. |
| 6,432,038 B1 | 8/2002 | Bakane |
| 6,432,040 B1 | 8/2002 | Meah |
| 6,443,887 B1 | 9/2002 | Derus et al. |
| 6,464,999 B1 | 10/2002 | Huo et al. |
| 6,533,719 B2 | 3/2003 | Kuyava et al. |
| 6,652,449 B1 | 11/2003 | Gross et al. |
| 6,659,937 B2 | 12/2003 | Polsky et al. |
| 6,689,046 B2 | 2/2004 | Sayet et al. |
| 6,712,772 B2 | 3/2004 | Cohen et al. |
| 6,723,042 B2 | 4/2004 | Aimli et al. |
| 6,730,017 B2 | 5/2004 | Henkel et al. |
| 6,749,556 B2 | 6/2004 | Banik |
| 6,862,480 B2 | 3/2005 | Cohen et al. |
| 6,896,651 B2 | 5/2005 | Gross et al. |
| 6,915,165 B2 | 7/2005 | Forsell |
| 6,921,360 B2 | 7/2005 | Banik |
| 6,935,847 B2 | 8/2005 | Kuyava et al. |
| 6,991,601 B2 | 1/2006 | Kuyava et al. |
| 7,128,707 B2 | 10/2006 | Banik |
| 7,169,103 B2 | 1/2007 | Ling et al. |
| 7,244,227 B2 | 7/2007 | Morningstar |
| 7,250,026 B2 | 7/2007 | Kuyava |
| 7,350,538 B2 | 4/2008 | Kuyava et al. |
| 7,387,603 B2 | 6/2008 | Gross et al. |
| 7,400,926 B2 | 7/2008 | Forsell |
| 7,407,482 B2 | 8/2008 | Kuyava |
| 8,545,391 B2 * | 10/2013 | Kuyava et al. ............... 600/38 |
| 8,864,651 B2 * | 10/2014 | Kuyava et al. ............... 600/38 |
| 9,005,111 B2 * | 4/2015 | Kuyava et al. ............... 600/38 |
| 2004/0167574 A1 | 8/2004 | Kuyava et al. |
| 2005/0075534 A1 | 4/2005 | Kuyava |
| 2005/0192633 A1 | 9/2005 | Montpetit |
| 2009/0132043 A1 | 5/2009 | George et al. |

OTHER PUBLICATIONS

U.S. Appl. No. 61/140,173, filed Dec. 23, 2008.
U.S. Appl. No. 61/140,350, filed Dec. 23, 2008.
Prosecution history from U.S. Appl. No. 12/644,805 including Non-Final Rejection mailed Mar. 22, 2013.
Office Action from related U.S. Appl. No. 14/037,797, mailed Mar. 27, 2014.
Office Action from related U.S. Appl. No. 14/337,926, mailed Sep. 30, 2014.

\* cited by examiner

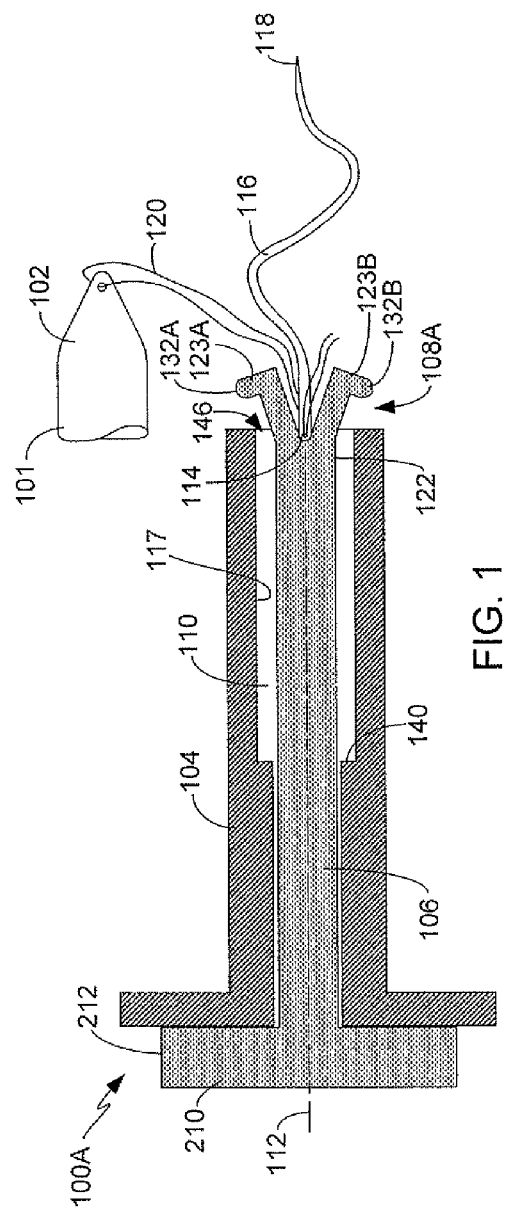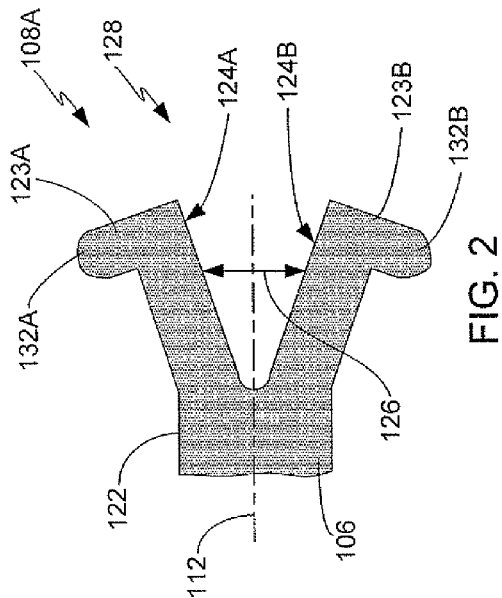

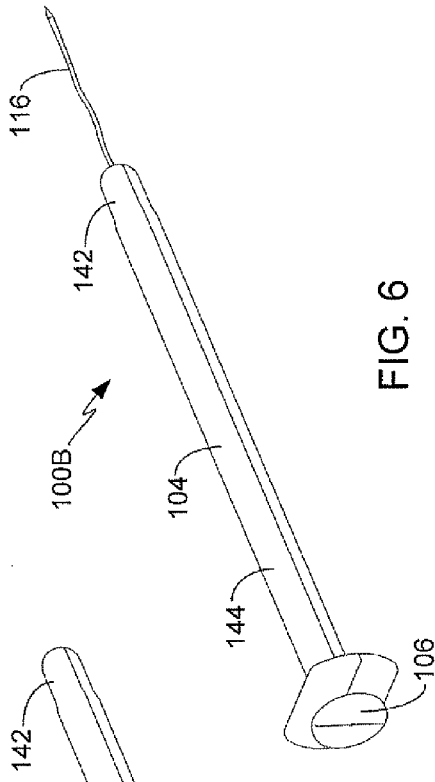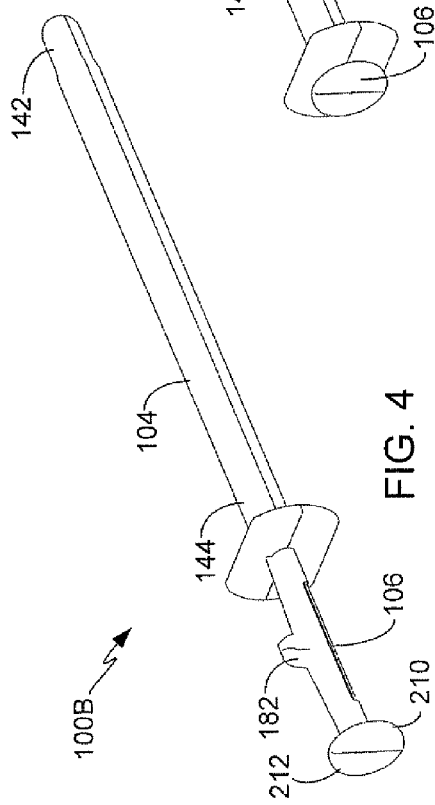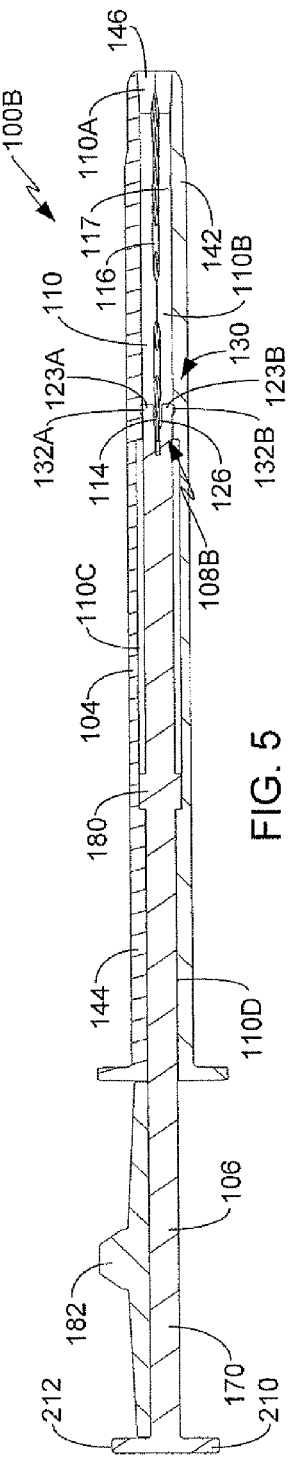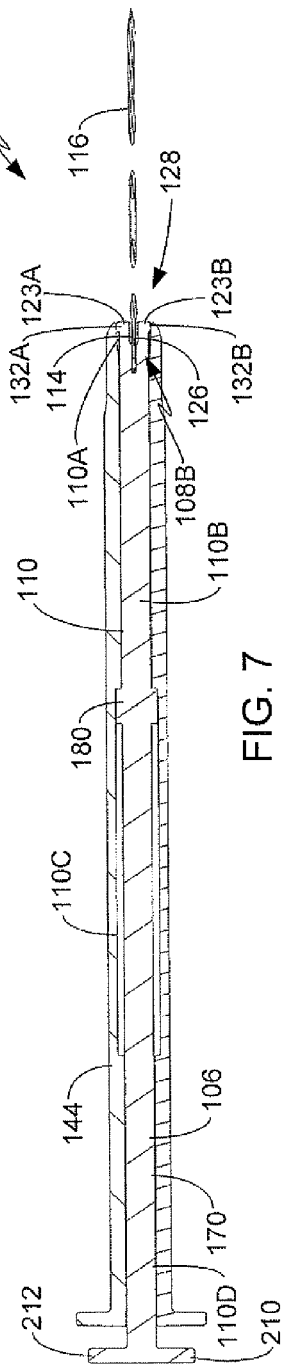
FIG. 6
FIG. 4
FIG. 5
FIG. 7

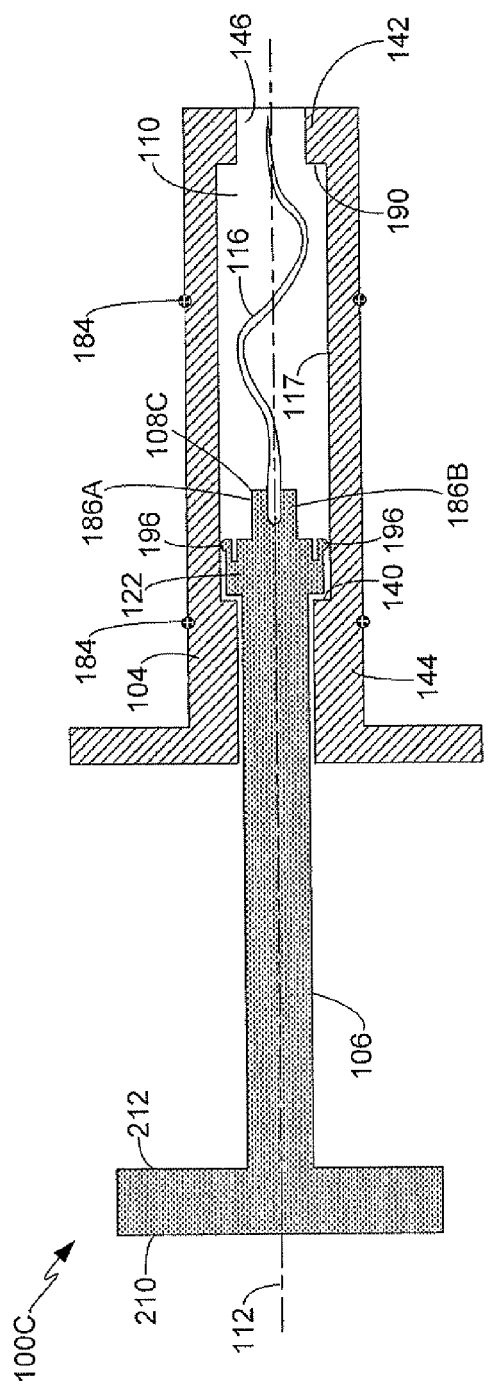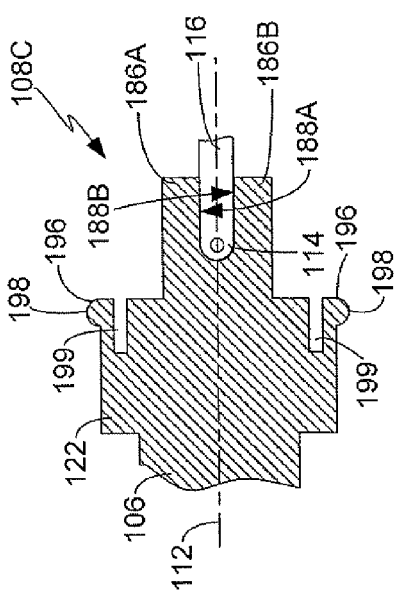
FIG. 8
FIG. 9

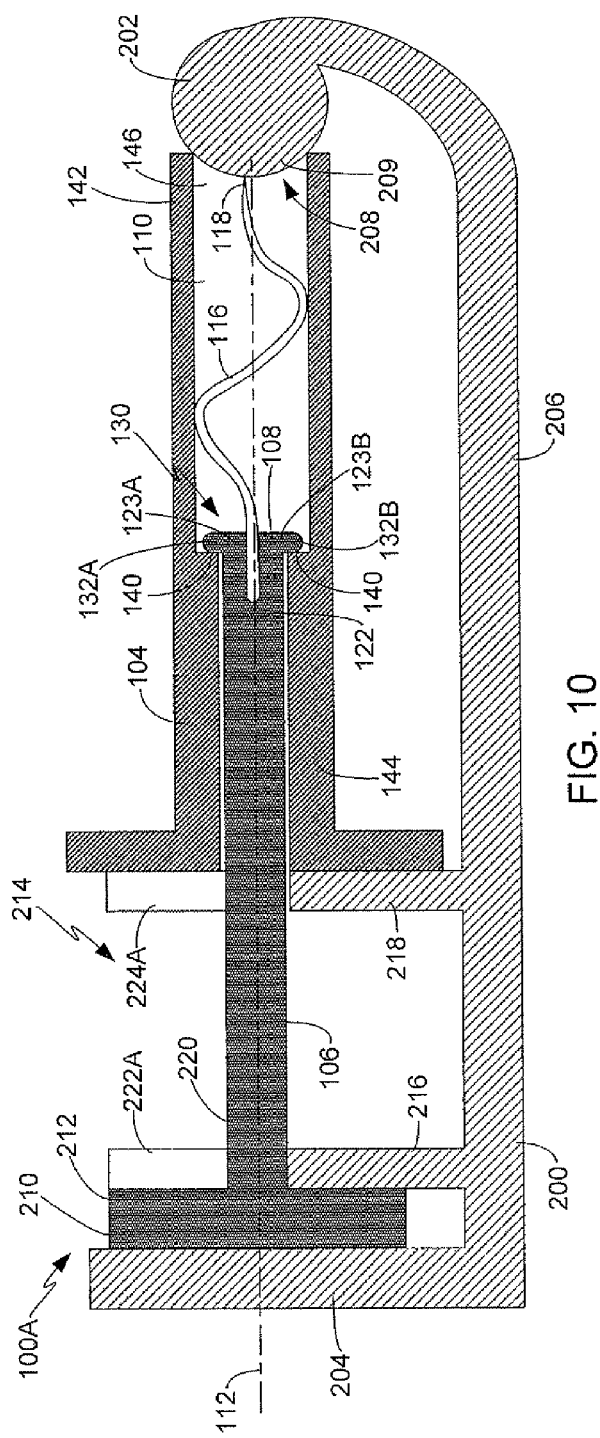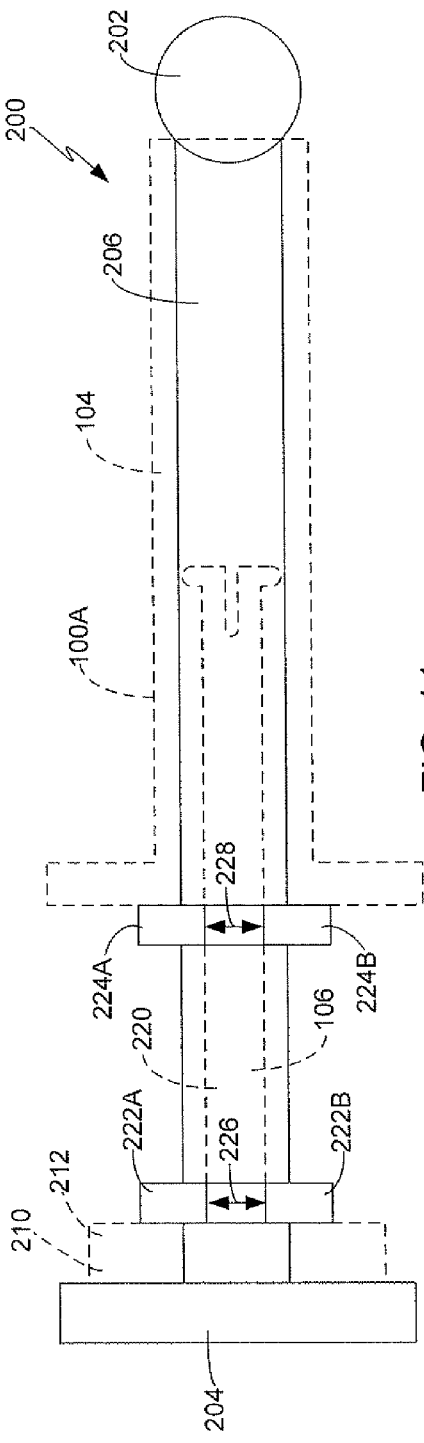

PENILE PROSTHESIS IMPLANTATION DEVICE

CROSS-REFERENCE TO RELATED APPLICATION

The present application is a continuation of U.S. patent application Ser. No. 14/337,926, filed Jul. 22, 2014, which is a continuation of U.S. patent application Ser. No. 14/037,797, filed Sep. 26, 2013, now U.S. Pat. No. 8,864,651, which is a continuation of U.S. patent application Ser. No. 12/644,805, filed Dec. 22, 2009, now U.S. Pat. No. 8,545,391, which is based on and claims the benefit of U.S. provisional patent application Ser. No. 61/140,173, filed Dec. 23, 2008 and U.S. provisional patent application Ser. No. 61/140,350, filed Dec. 23, 2008. The above-referenced applications are hereby incorporated by reference in their entirety.

BACKGROUND

The present disclosure relates to medical devices used in implant surgery. More specifically, the present disclosure relates to a penile prosthesis implantation device used to assist in the implantation of penile prostheses cylinders in the corpus cavernosae of a patient. In some instances, these cylinders are inflatable, which are connected to a fluid-filled reservoir with a pump and valve assembly. Another type of cylinder is non-inflatable and does not require the pump and valve assembly.

The penile implantation operation is an invasive treatment. To reach the corpus cavernosae and implant the cylinders, the surgeon will first make an incision at the base of the penis, such as where it meets the scrotum. The patient is prepared for the cylinders by dilating each corpus cavernosum.

Once the patient has been prepared, the surgeon will insert a medical device known as a Furlow insertion tool with a Keith needle into the dilated corpus cavernosum. The Furlow tool is a well known and often used device in the art and is described in U.S. Pat. No. 4,244,370, which was filed in 1978. The Furlow tool is a long slender device having a hollow barrel with a plunger device known as an obturator at the rearward end. The Keith needle is also a well-known article used in many areas of medicine. The Keith needle looks like a heavy sewing needle and is used to pierce tissue. The Keith needle fits within the barrel of the Furlow tool and is ejected from the forward end with the obturator.

In order to install the penile prosthesis cylinder in one of the corpus cavernosum, the Keith needle is attached to a suture that is also attached to the cylinder. The Keith needle with a threaded suture is then inserted into the distal opening of the Furlow tool. The Furlow tool is advanced into the corpus cavernosum until the forward end is inside of the crown of the penis, or glans. At this point, the cylinder and part of the suture attached to the cylinder remain outside of the patient's body. The Furlow tool is used to force the Keith needle out of the barrel and through the glans. The surgeon grasps the Keith needle from outside of the body and pulls it from the penis leaving the suture threaded through the corpus cavernosum. The Furlow tool is withdrawn from the penis. The suture is then pulled to draw the cylinder into the incision and the corpus cavernosum. Once the implant is in place, the suture is removed. This procedure is then performed again on the other corpus cavernosum.

Problems with the above-described system include the numerous opportunities for medical personnel, the patient, or an inflatable penile prosthesis to become pierced by the Keith needle. For example, medical personnel must handle the Keith needle while threading the suture through the eye of the Keith needle and during insertion of the needle into the Furlow tool. Additionally, while the Keith needle provides a slight interference fit within the barrel of the Furlow tool, it may also fall out during handling, thereby presenting additional opportunities for medical personnel, the patient or the penile prosthesis to become pierced by the Keith needle. Also, threading the suture through the eye of the Keith needle lengthens surgical time, increasing the chance of infection, and can be a source of frustration for the surgeon when threading the suture is difficult.

The discussion above is merely provided for general background information and is not intended to be used as an aid in determining the scope of the claimed subject matter.

SUMMARY

Embodiments of the invention are generally directed to a penile prosthesis implantation device. One embodiment of the penile prosthesis implantation device comprises a barrel having a bore, an obturator and a needle clamp. The obturator has a longitudinal axis, a first end and a second end. The second end of the obturator is adapted for slidable insertion into the bore of the barrel. The needle clamp is coupled to the second end of the obturator and comprises first and second pinching surfaces that are separated by a gap.

Another embodiment of the invention is directed to a needle guard that attaches to the penile prosthesis implantation device that includes a barrel having a bore, an obturator having a first end and a second end, the second end adapted for slidable insertion into the bore and a needle within the bore adjacent the second end of the obturator. The needle guard generally operates to secure a needle within the barrel of the device. One embodiment of the needle guard comprises first, second and third members. The first member is configured to cover an end of the barrel at which the bore is exposed. The second member is configured to engage the first end of the obturator. The third member is coupled to the first and second members of the needle guard.

Yet another embodiment of the invention is directed to a kit comprising a penile prosthesis implantation device, a penile prosthesis, a suture and packaging. The device includes a barrel having a bore, an obturator, a needle clamp and a needle. The obturator has a longitudinal axis, a first end and a second end, which is adapted to slide within the bore. The needle clamp is located at the second end of the obturator and comprises first and second pinching surfaces separated by a gap. The needle has a connecting end that is held between the first and second pinching surfaces, and a pointed tip opposite the connecting end. The needle is recessed within the bore adjacent an end of the barrel. The suture has a first end connected to the connecting end of the needle, and a second end connected to the penile prosthesis. The packaging contains the device, the penile prosthesis, and the suture.

BRIEF DESCRIPTION OF THE DRAWINGS

FIG. 1 is a cross-sectional view of a penile prosthesis implantation device in accordance with embodiments of the invention.

FIG. 2 is a magnified cross-sectional view of a needle clamp of the device of FIG. 1.

FIGS. 4 and 5 respectively are isometric and cross-sectional views of a penile prosthesis implantation device, formed in accordance with embodiments of the invention, in a retracted position.

FIGS. 6 and 7 respectively are isometric and cross-sectional views of a penile prosthesis implantation device, formed in accordance with embodiments of the invention, in an extended position.

FIG. 8 is a cross-sectional view of a penile prosthesis implantation device in accordance with embodiments of the invention.

FIG. 9 is a magnified view of a needle clamp of the device of FIG. 8.

FIG. 10 is a cross-sectional view of a needle guard in accordance with embodiments of the invention.

FIG. 11 is a top plan view of a needle guard in accordance with embodiments of the invention.

DETAILED DESCRIPTION OF ILLUSTRATIVE EMBODIMENTS

Figure 3:
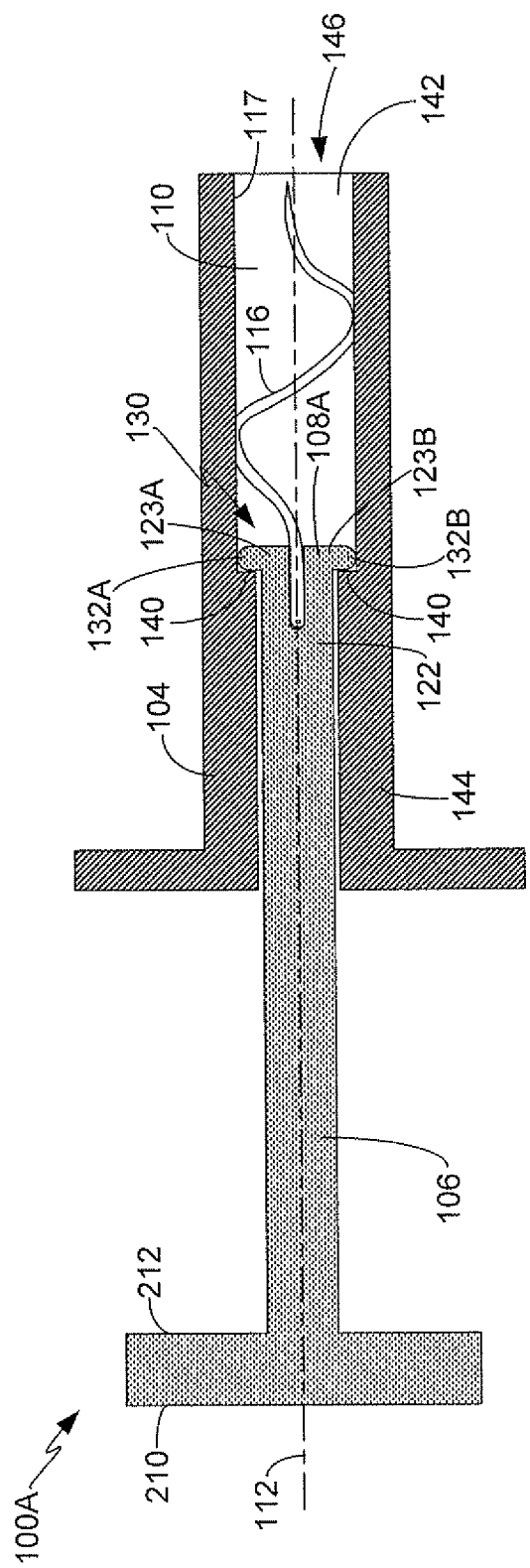
FIG. 3 is a side cross-sectional view of a needle clamp in a clamping position in accordance with embodiments of the invention.

FIG. 1 is a cross-sectional view of a penile prosthesis implantation device 100A in accordance with embodiments of the invention. The device 100A is configured for the use in the insertion of a penile prosthesis 101, a tip end 102 of which is shown in FIG. 1, into the corpus cavernosa of the penis of a patient for the treatment of impotence, in a similar manner as that described above. One embodiment of the device 100A comprises a barrel 104, an obturator 106 and a needle clamp 108A. The barrel 104 has a bore 110 that is generally axially aligned with a longitudinal axis 112 of the obturator 106. In accordance with one embodiment, most of the components of the device 100A are formed of plastic.

The needle clamp 108A is configured to grasp a thread attachment or connecting end 114 of a needle 116, such as a Keith needle. Embodiments of the needle 116 include various shapes, such as straight, crooked like a lightning bolt as shown in FIG. 1, or other desired shape. In one embodiment, the barrel 104 is designed such that the needle 116 fits inside the bore 110 with a light interference with the interior surface 117 of the bore. In one embodiment, friction between the needle 116 and the surface 117 preferably holds the needle 116 within the bore 110 during normal handling of the device 100A.

The needle 116 includes a piercing end 118 used to pierce the glans of the penis. In one embodiment, a suture 120 is coupled to the thread attachment end 114 of the needle 116 and the tip end 102 of the penile prosthesis 101. In one embodiment, this coupling of the suture 120 to the thread attachment end 114 and the tip end 102 of the penile prosthesis is performed in accordance with the method described in U.S. Pat. No. 7,407,482, which is incorporated herein by reference in its entirety.

The needle clamp 108A is either attached to, or formed integral with, a distal end 122 of the obturator 106. One embodiment of the clamp 108A comprises pinching members 123A and 123B respectively having opposing pinching surfaces 124A and 124B, which are best shown in the magnified cross-sectional view of the needle clamp 108A provided in FIG. 2. The pinching surfaces 124A and 124B are separated by gap 126.

In general, the needle clamp 108A includes a receiving position 128, in which the needle clamp 108A is poised to receive the thread attachment end 114 of the needle 116, as shown in FIGS. 1 and 2. In one embodiment, the needle clamp 108A is positioned in the receiving position 128 in response to the extension of the needle clamp 108A outside of the barrel 104, as shown in FIG. 1. In one embodiment, the pinching members 123A and 123B are biased such that they separate from each other in the radial direction relative to the longitudinal axis 112 when the clamp 108A is moved to the receiving position 128.

The clamp 108A also includes a clamping position 130, which is illustrated in the side cross-sectional view of FIG. 3. Note that the sutures 120 and the penile prosthesis 101 (FIG. 1), which may be attached to the needle 116, are not shown in FIG. 3 in order to simplify the illustration. When the needle clamp 108A is moved from the receiving position 128 to the clamping position 130, the pinching members 123A and 123B are biased toward each other in the radial direction relative to the longitudinal axis 112 such that the corresponding pinching surfaces 124A and 124B pinch the thread attachment end 114 of the needle 116 and secure the needle 116 to the obturator 106.

In one embodiment, the needle clamp 208A comprises at least one deflector portion, such as deflector portion 132A or 132B, that is axially displaced from the longitudinal axis 112 of the obturator 106. When the needle clamp 108A is in the receiving position 128, the deflector portions 132A and 132B are positioned outside of the barrel 104, as shown in FIGS. 1 and 2. The needle clamp 108A is moved to the clamping position 130 by sliding the obturator 106 relative to the barrel 104 in the axial direction to pull the deflector portions 132A and 132B within the bore 110 of the barrel 104, which in turn drives the pinching members 123A and 123B toward each other in the radial direction to move the needle clamp 108A into the clamping position 130, as shown in FIG. 3.

Thus, the engagement of the deflector portions 132A and 132B with the interior surface 117 of the barrel 104 biases the first and second pinching surfaces 124A and 124B toward each other as the clamping member moves from the receiving position 128 to the clamping position 130. This movement of the pinching members 123A and 123B also causes a reduction in a length of the gap 126 between the pinching surfaces 124A and 124B as the clamp 108A moves from the receiving position 128 to the clamping position 130. This reduction in the length of the gap 126 causes the thread attachment end 114 of the needle 116 to be pinched by the surfaces 124A and 124B thereby securing the needle 116 within the clamp 108A.

While the needle 116 is secured within the clamp 108A, the needle 116 along with the suture 120 can be held within the bore 110 of the barrel 104 until it is necessary to deploy the needle, such as after the piercing end 118 is passed through the glans of the penis. The needle 116 can be released by moving the obturator 106 in the axial direction to place the clamp 108A in the receiving position 128. This allows the needle 116 to be pulled through the glans of the penis, for example.

In one embodiment, the barrel 104 includes a stop portion or member 140 that protrudes within the bore 110 and restricts the axial movement of the obturator 106, as shown in FIG. 3. In one embodiment, the barrel 104 comprises first and second ends 142 and 144. The internal diameter of the bore in the first end 142 is greater than the internal diameter of the bore 110 in the second end 144. The reduction in the diameter of the bore 110 from the first end 142 to the second end 144 forms the stop 140. In one embodiment, the deflector portions 132A and 132B engage the stop member 140 to prevent further axial movement of the obturator 106 and clamp 108A along the longitudinal axis 112 in the direction that is toward the second end 144 of the barrel 104.

In operation, the obturator 106 is slid within the barrel 104 through an opening 146 at the first end 142 such that the deflector portions 132A and 132B extend beyond the bore 110. This places the clamp 108A in the release position 128, in which the pinching members 123A and 123B as well as the corresponding pinching surfaces 124A and 124B are separated, as shown in FIGS. 1 and 2. The thread attachment end 114 of the needle 116, which is coupled to the tip end 102 of the penile prosthesis by the suture 120, is received within the gap 126. The obturator 106 is then slid within the barrel 104 along the longitudinal axis toward the second end 144 such that the clamp 108A is retracted within the bore 110 at the first end 142 of the barrel 104. This causes the deflector portions 132A and 132B to engage the interior surface 117 of the barrel 104 and deflect the pinching members 123A and 123B radially causing the gap 126 to be reduced and the pinching surfaces 124A and 124B to pinch the thread attachment end 114 of the needle 116. With the needle 116 secured between the pinching surfaces 124A and 124B of the clamp 108A, the obturator 106 pulls the needle 116 and the attached suture 120 within the first end 142 of the barrel 104, as shown in FIG. 3. When the deflector portions 132A and 132B engage the stop members 140 of the barrel 104, the needle is preferably fully received within the bore 110 of the barrel 104. This is considered the fully retracted position.

When the needle is delivered through the glans penis during the implantation of a penile prosthesis, the obturator 106 is slid relative to the barrel 104 from the retracted position to move the clamp 108A into the release position 128, which allows the needle to be released and easily pulled through the penis.

FIGS. 4-7 illustrate a penile prosthesis implantation device 100B in accordance with additional embodiments of the present invention. Elements of the device 100B shown in FIGS. 4-7 that are identified by the same or similar numbers used to identify elements in FIGS. 1-3 correspond to the same or similar elements. FIGS. 4 and 5 respectively are isometric and cross-sectional views of the penile prosthesis implantation device 100B while in a retracted position, in which the needle 116 is retracted within the bore 110 of the barrel 104. FIGS. 6 and 7 respectively are isometric and cross-sectional views of the penile prosthesis implantation device 100 while in an extended position, in which the needle 116 is extended beyond the barrel 104.

As with the device 100A, the device 100B is configured for use in the insertion of a penile prosthesis into the corpus cavernosae of the penis of a patient for the treatment of impotence, as described above. One embodiment of the device 100B comprises a barrel 104, an obturator 106 and a needle clamp 108B. The barrel 104 has a bore 110 that is generally axially aligned with a longitudinal axis 112 of the obturator 106.

In one embodiment of the device 100B, the bore 110 of the barrel 104 comprises a tapered section 110A at the opening 146. The tapered section 110A of the bore 110 has an internal diameter that increases with distance traveled along the longitudinal axis 112 toward the opening 146. As the device 100 is moved from the retracted position (FIGS. 4 and 5) to the extended position (FIGS. 6 and 7) by moving the clamp 108B toward the opening 146 of the barrel 104, the needle clamp 108B opens to the receiving position 128, shown in FIG. 7. While in the receiving position 128, the deflector portions 132A and 132B are positioned within the tapered section 110A of the bore 110. The larger internal diameter in the section 110A allows the deflector portions 132A and 132B to expand slightly within the bore 110 thereby increasing the gap between the pinching members 123A and 123B.

In one embodiment, the gap between the pinching members 123A and 123B allows for an interference fit between the thread attachment end 114 of the needle 116 while the needle clamp 108B is in the receiving position 128. The thread attachment end 114 can be secured to the needle clamp 108B by the interference fit between the pinching members 123A and 123B. One advantage to this receiving position 128 is that one may attach the thread attachment end 114 of the needle 116 to the needle clamp 108B without having to retract the obturator 106.

As the obturator 106 is moved relative to the barrel 104 toward the retracted position, the deflector portions 132A and 132B are compressed by the narrowing of the internal diameter of the bore 110 as the needle clamp 108B is moved from the tapered section 110A to section 110B of the bore 110, which has a narrower internal diameter. The compression of the deflector portions 132A and 132B within the section 110B of the bore 110 drives the pinching members 123A and 123B toward each other thereby narrowing the gap between the pinching members 123A and 123B and securing the thread attachment end 114 of the needle 116 within the needle clamp 108B. Accordingly, the needle clamp 108B moves to this clamping position 130 as the device 100 moves from the extended position to the retracted position. In one embodiment, the needle 116 is fully received within the bore 110 of the barrel 104 when the device 100 is the fully retracted position shown in FIGS. 4 and 5.

In accordance with another embodiment, the obturator 106 includes a stop member 180 positioned, for example, intermediate a proximal end 210 and the needle clamp 108B. Additionally, the bore 110 includes a section 110C having an internal diameter that accommodates the stop member 180. The section 110B located at the first end 142 of the barrel 104 and a section 110D located at the second end 144 of the barrel 104 have internal diameters that are smaller than the internal diameter of the section 110C of the bore 110. Additionally, the stop member 180 is sized to prevent it from entering the sections 110B or 110D of the bore 110. As a result, the stop member 180 limits the distance the obturator 106 can be moved relative to the barrel 104 between the fully retracted position shown in FIG. 5 and the fully extended position shown in FIG. 7. In one embodiment, the needle clamp 108B is positioned within the tapered section 110A of the bore 110 when the device 100 is positioned in the fully extended position, as shown in FIG. 7.

One embodiment of the device 100B includes a protective member 182 that snaps to the shaft 170 of the obturator 106 while the device 100 is in the fully retracted position, as shown in FIGS. 4 and 5. The protective member 182 operates to prevent the obturator 106 from moving from the retracted position to the extended position and thereby prevents the needle 116 from being unintentionally extended out of the barrel 104. Other similar devices for use with the penile prosthesis implantation devices of the present invention are described below.

FIG. 8 is a cross-sectional view of a penile prosthesis implantation device 100C in accordance with additional embodiments of the invention. The elements illustrated in FIG. 8 and other figures having the same or similar labels as the elements of FIGS. 1-7 generally correspond to the same or similar elements. FIG. 9 is a magnified view of the needle clamp 208C shown in FIG. 8. As with the devices 100A and 100B, the device 100C is configured for use in the insertion of a penile prosthesis into the corpus cavernosae of the penis of a patient for the treatment of impotence, as described above.

Accordingly, the sutures 120 and the penile prosthesis 101 (FIG. 1) may be attached to the needle 116 held by the device 100C, but are not shown in order to simplify the illustrations.

One embodiment of the device 100C comprises a barrel 104, an obturator 106 and a needle clamp 108C. The barrel 104 has a bore 110 that is generally axially aligned with a longitudinal axis 112 of the obturator 106. In one embodiment, the barrel 104 comprises separate halves that are secured together using one or more o-rings 184 (shown in FIG. 8), one or more latches, an adhesive, ultrasonic welding, or other suitable technique.

The needle clamp 108C is configured to grasp the connecting end 114 of a needle 116 formed in accordance with the embodiments described above. The needle clamp 108C is either attached to, or formed integral with, a distal end 122 of the obturator 106. One embodiment of the clamp 108C comprises pinching members 186A and 186B respectively having opposing pinching surfaces 188A and 188B, which are best shown in the magnified cross-sectional view of the needle clamp 108C provided in FIG. 9. The pinching surfaces 188A and 188B are separated by a gap, which is configured to receive the thread attachment end 114 of the needle 116, as shown. The gap between the pinching surfaces 188A and 188B is preferably selected to be slightly smaller than the thickness of the end 114 of the needle 116 to provide an interference fit between the pinching surfaces 188A and 188B and the end 114 of the needle 116. Frictional resistance between the pinching surfaces 188A and 188B and the end 114 of the needle 116 caused by the interference fit operates to secure the end 114 of the needle 116 in the needle clamp 108C during normal use of the device 100C including handling the device 100C and piercing the glans of the penis with the end 118 of the needle 116 during a penile prosthesis implantation operation. In one embodiment, the end 114 of the needle 116 can be inserted within the gap between the pinching surfaces 188A and 188B by hand.

In one embodiment, the barrel 104 includes a stop member 140 at the second end 144 of the bore 110, such as a shoulder portion, that engages a portion of the distal end 122 of the obturator 106 to prevent the distal end 122 of the obturator 106 from being pulled out of the end 144 of the barrel 104. In accordance with another embodiment, the barrel 104 includes a stop member 190 at the first end 142 of the bore 110, such as a shoulder portion, that engages a portion of the distal end 122 of the obturator 106 to limit the distance the obturator 106 can travel toward the end 142 of the barrel 104.

One embodiment of the obturator 106 includes one or more bore engaging members 196, embodiments of which are shown in FIG. 9. The one or more bore engaging members 196 are configured to engage the interior wall 117 of the bore 110 and provide frictional resistance between the obturator 106 and the barrel 104. The frictional resistance between the bore engaging members 196 and the interior wall 117 of the barrel 104 operates to prevent undesired movement of the obturator 106 relative to the barrel 104 during normal handling of the device 100C. When the needled 116 secured by the clamp 108C is retracted within the barrel 104, as illustrated in FIG. 8, the frictional resistance prevents the obturator 106 from sliding relative to the barrel 104 and extending the needle 116 outside of the barrel 104.

In one embodiment, the bore engaging member or members 196 include a surface 198 that is radially displaced from the axis 112 a greater distance than other portions of the distal end 122 of the obturator 106. In one embodiment, a gap 199 is formed between the bore engaging member 196 and the interior portion of the distal end 122 of the obturator 106. The gap 199 allows the bore engaging member 196 to deflect toward the central axis 112 responsive to contact between the surfaces 198 and the surface 117 of the bore 110. In one embodiment, the bore engaging members 196 flex toward the axis 112 when installed within the bore 110 of the barrel 104. The pressure applied to the interior wall 117 of the bore 110 by the surface 198 of the one or more bore engaging members 196 generates the desired frictional resistance between the obturator 106 and the barrel 104. In one embodiment, the one or more bore engaging members 196 comprises a ring-shaped member that is generally coaxial to the axis 112. Alternatively, the bore engaging members 196 may comprise a plurality of components that are angularly displaced about the axis 112.

Another embodiment of the invention is directed to a needle guard that is configured to secure the needle 116 within the bore 110 of a prosthesis implantation device, such as the devices 100A-C described above. While the embodiments of the needle guard will be illustrated as being applied to the device 100A, it is understood that embodiments of the needle guard 200 may also be used with the devices 100B and 100C, or other similar device, in the same or similar manner.

FIG. 10 is a cross-sectional view of a needle guard 200 in accordance with embodiments of the invention. It is understood that the end 114 of the needle 116, installed within the barrel 104, may be coupled to sutures 120 that are connected to a penile prosthesis 101, as shown in FIG. 1. These elements are not shown in order to simplify the illustration.

In one embodiment, the needle guard 200 is formed of plastic. The attachment of the needle guard 200 to the device 100 operates to cover the open end 142 of the barrel 104 to prevent the piercing end 118 of the needle 116 from sticking out. In one embodiment, the needle guard 200 cradles the obturator 106 to prevent it from advancing the needle 116 through the opening in the end 142 of the barrel 104.

One embodiment of the needle guard 200 comprises a first member 202, a second member 204 and a third member 206. The first member 202 is configured to cover the opening 208 of the bore 110 at the first end 142. In one embodiment, the first member comprises a surface 209, such as a convex surface, that partially extends within the bore 110 of the barrel 104. The second member 204 engages a first end 210 of the obturator 106 and the third member 206 couples the first and second members of the needle guard 200 together.

In one embodiment, the obturator 106 includes a cross member 212 at the first end 210 that extends transversely from the longitudinal axis 112, and the second member 204 of the needle guard 200 engages the cross member 212, as shown in FIG. 10. In one embodiment, the first and second members 202 and 204 include portions that are inline with the longitudinal axis 112 of the obturator 106. In one embodiment, the needle guard 200 is partially secured to the device 100 through the application of a compressive force between the first and second members 202 and 204 that is applied to the obturator 106 and the barrel 104.

One embodiment of the needle guard 200 includes a fourth member 214 that is positioned between the cross member 212 and the barrel 104, as shown in FIG. 10. The fourth member is configured to limit movement of the obturator 106 toward the barrel 104 along the longitudinal axis 112. As a result, one embodiment of the needle guard 200 operates to prevent relative movement between the obturator 106 and the barrel 104. One embodiment of the fourth member 214 comprises a portion 216 that engages the cross member 212 of the obturator and a portion 218 that engages the barrel 104. While illustrated as being integral with or coupled to third member 206, it is understood that the fourth member 214 can be formed as a separate component (i.e., non-integral to the needle guard 200) that fits between the barrel 104 and the cross member 212.

In accordance with one embodiment, the fourth member 214 is secured between the cross member 212 and the barrel 104 due to an interference fit there-between. In accordance with another embodiment, the fourth member 214 is configured to snap-fit to the shaft 220 of the obturator 106, as illustrated in the top plan view of the needle guard 200 shown in FIG. 11 with the obturator 106 and the barrel 104 illustrated in phantom lines. In one embodiment, the fourth member 214 includes at least two opposing clip members such as clip member pair 222A and 222B extending from portion 216, or clip member pair 224A and 224B extending from portion 218. The gap 226 separating clip member pair 222A and 222B or gap 228 separating clip member pair 224A and 224B is set such that the shaft 220 of the obturator 106 can be secured between the clip member pairs 222A and 222B and/or 224A and 224B by an interference-fit.

Figure 12:
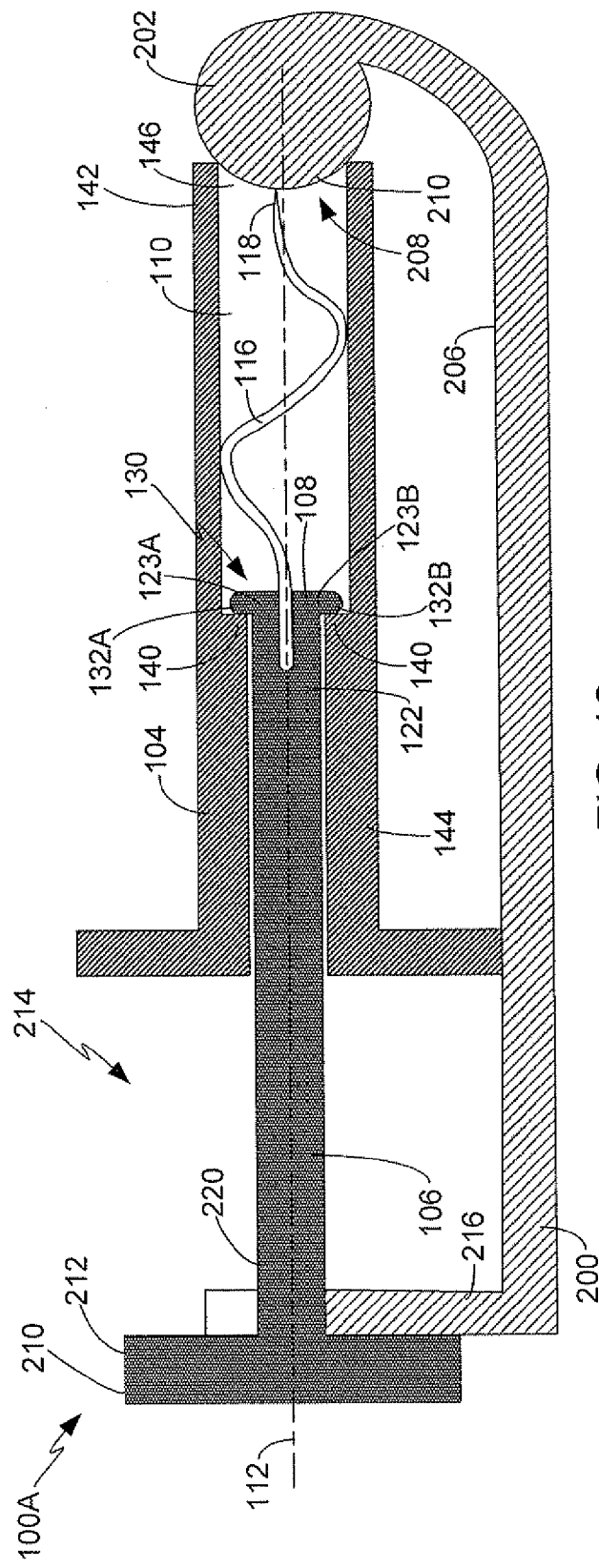
FIG. 12 is a cross-sectional view of a needle guard in accordance with embodiments of the invention.

FIG. 12 is a side view of the needle guard 200 in accordance with another embodiment of the invention. This embodiment of the needle guard 200 takes advantage of the stop member 140 (devices 100A and 100C) of the barrel 104 which prevents the obturator 106 from being pulled out of the second end 144 of the barrel 104. The device 100 is secured to the needle guard 200 using the first member 202, the third member 206 and the fourth member 214. In one embodiment, the portion 216 includes the clip members 222A and 222B (not shown) to provide the desired snap-fit or interference fit to the shaft 220 of the obturator 106.

Figure 13:
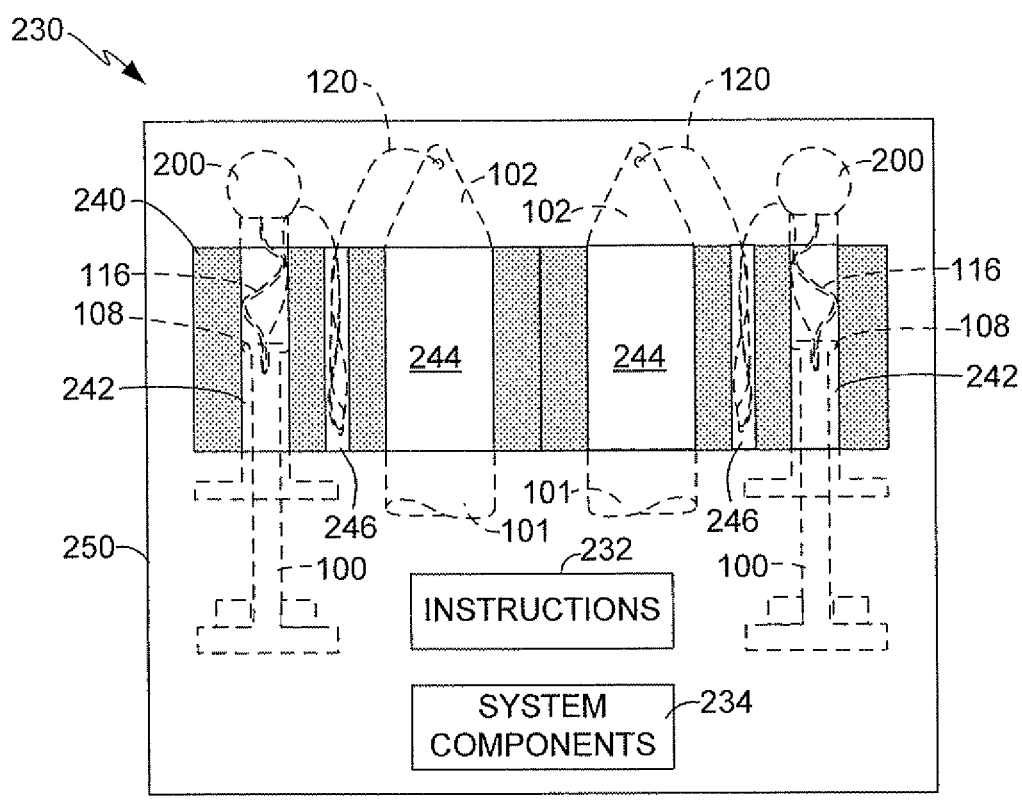
FIG. 13 is a schematic diagram of a kit in accordance with embodiments of the invention.

One embodiment of the invention relates to a kit 230, embodiments of which are illustrated in the schematic diagram of FIG. 13. One embodiment of the kit 230 includes one or more penile implantation devices 100 formed in accordance with one or more of the embodiments described above. In one embodiment, the device 100 holds a needle 116 in the needle clamp 108 formed in accordance with one or more of the embodiments described above. In one embodiment, the needle 116 is threaded with a suture 120 and coupled to a tip end 102 of the penile prosthesis 101. The obturator 106 is placed in the retracted position, in which the needle 116 is fully received within the barrel 104. In one embodiment, a needle guard 200, formed in accordance with one or more embodiments described above, is installed on the device 100. In one embodiment, the kit contains instructions 232 for using the device 100 to implant the penile prosthesis. In one embodiment, system components 234, such as pumps, fluid reservoirs and other components used in penile prosthetic systems are also included in the kit 230.

In one embodiment, a device holder 240 is used to attach one or more of the devices 100, penile prosthesis 101, and/or sutures 120 together, as illustrated in FIG. 13. In one embodiment, the device holder 240 includes at least one device receiving portion 242, such as a slot or a bore, configured to receive, or attach to, a device 100. The device 100 is preferably sufficiently held by the portion 242 to allow for normal handling of the device holder 240 while allowing the device 100 to be removed from the portion 242 by hand. In one embodiment, the device holder 240 includes at least one prosthesis receiving portion 244 configured to receive a penile prosthesis 101, such as a slot or a bore. The penile prosthesis 101 is preferably sufficiently held by the portion 244 to allow for normal handling of the device holder 240 while allowing the penile prosthesis 101 to be removed from the portion 242 by hand.

In one embodiment, the device holder is formed using a silicone elastomer. Some advantages of such a material include its elasticity and ability to accommodate the device and prosthesis, its biocompatibility, and its ability to be easily sterilized by common methods.

In one embodiment, the device holder 240 includes at least one suture receiving portion 246 configured to receive the suture 120, such as a slot or a bore. The suture 120 is preferably sufficiently held by the portion 246 to allow for normal handling of the device holder 240 while allowing the suture 120 to be removed from the portion 242 by hand. In one embodiment, the portion 246 is in the form of a bore and the suture 120 is wrapped up and inserted into the bore. When the device 100 and prosthesis 101 are removed from the portions 242 and 244, the suture 120 can be pulled from the portion 246 without tangling the suture 120. Additionally, portion 246 is used to hold the suture 120 to prevent it from becoming tangled with the other components of the kit 230 during shipment and handling.

In one embodiment, the kit 230 includes packaging 250 that contains one or more of the components of the kit 230 described above. The components of the kit 230 are preferably sterilized in the packaging 250. The packaging 250 is then sealed.

Although the present invention has been described with reference to preferred embodiments, workers skilled in the art will recognize that changes may be made in form and detail without departing from the spirit and scope of the invention.

What is claimed is:

1. A penile prosthesis implantation device comprising:
   a barrel having a bore; and
      an obturator received within the bore and configured to slide along a longitudinal axis of the bore relative to the barrel, the obturator comprising:
         a needle clamp including one or more pinching members extending from a distal end of the obturator along the longitudinal axis, wherein the one or more pinching members include pinching surfaces that are configured to hold a thread attachment end of a needle; and
         one or more bore engaging members at the distal end of the obturator, the one or more bore engaging member having a surface that engages an interior wall of the bore; and
         a gap extending between a central portion of the obturator and the one or more bore engaging members;
      wherein the one or more bore engaging members deflect toward the central portion and the longitudinal axis in response to contact with the interior wall of the bore independently from the one or more pinching members and the pinching surfaces.

2. The device of claim 1, wherein the needle clamp comprises a receptacle between the pinching surfaces that is configured to receive a thread attachment end of a needle and hold the end of the needle through an interference fit with the pinching surfaces.

3. The device of claim 1, wherein the needle clamp extends from the central portion along the longitudinal axis.

4. The device of claim 1, wherein the surface of each of the one or more bore engaging members is radially displaced from the longitudinal axis a greater distance than the needle clamp.

5. The device of claim 1, wherein the one or more bore engaging members comprise a ring-shaped member that is coaxial to the longitudinal axis.

6. The device of claim 1, further comprising a needle guard comprising:
   a first member covering an opening to the bore at a distal end of the barrel;

a second member engaging a proximal end of the obturator; and a third member coupled to the first and second members of the needle guard;

wherein the needle guard maintains the obturator in a retracted position within the bore.

7. The device of claim 1, wherein the one or more pinching members are displaced along the longitudinal axis from the one or more bore engaging members and the central portion of the obturator.

8. The device of claim 1, wherein the gap extends in a plane that is perpendicular to the longitudinal axis, and the longitudinal axis extends through a portion of the central portion that is within the plane.

9. The device of claim 8, wherein the one or more bore engaging members extend from the distal end of the obturator at a location that is displaced along the longitudinal axis toward a proximal end of the obturator from the one or more pinching members.

* * * * *